United States Patent [19]
Winston et al.

[11] Patent Number: 5,385,727
[45] Date of Patent: Jan. 31, 1995

[54] DENTIFRICES CONTAINING ZINC OXIDE PARTICLES AND SODIUM BICARBONATE

[75] Inventors: Anthony E. Winston, East Brunswick, N.J.; Todd W. Domke, Newtown, Pa.; Amy L. Joseph, Hopewell, N.J.

[73] Assignee: Church & Dwight Co., Inc., Princeton, N.J.

[21] Appl. No.: 64,409

[22] Filed: May 19, 1993

[51] Int. Cl.$^6$ .......................... A61K 7/16; A61K 7/18
[52] U.S. Cl. ........................ 424/49; 424/52; 424/57; 424/641; 424/642
[58] Field of Search ................. 424/49–58, 424/641, 642

[56] References Cited

U.S. PATENT DOCUMENTS

| | | | |
|---|---|---|---|
| 3,622,662 | 11/1971 | Roberts et al. | 424/54 |
| 3,624,199 | 11/1971 | Norfleet et al. | 424/57 |
| 3,989,814 | 11/1976 | Cordon et al. | 424/57 |
| 4,022,880 | 5/1977 | Vinson et al. | 424/49 |
| 4,082,841 | 4/1978 | Pader | 424/50 |
| 4,100,269 | 7/1978 | Pader | 424/49 |
| 4,138,477 | 2/1979 | Gaffar | 424/52 |
| 4,152,418 | 5/1979 | Pader | 424/50 |
| 4,154,815 | 5/1979 | Pader | 424/50 |
| 4,159,315 | 6/1979 | Wagenknecht, deceased et al. | 424/48 |
| 4,160,054 | 7/1979 | Wagenknecht, deceased et al. | 424/48 |
| 4,170,634 | 10/1979 | Cordon et al. | 424/49 |
| 4,187,288 | 2/1980 | Cordon et al. | 424/49 |
| 4,309,409 | 1/1982 | Coll-Palagos et al. | 424/52 |
| 4,339,432 | 7/1982 | Ritchey et al. | 424/54 |
| 4,375,958 | 3/1983 | Manhart | 433/217 |
| 4,425,324 | 1/1984 | Harvey et al. | 424/52 |
| 4,425,325 | 1/1984 | Harvey et al. | 424/54 |
| 4,455,293 | 6/1984 | Harvey et al. | 424/52 |
| 4,455,294 | 6/1984 | Harvey et al. | 424/52 |
| 4,459,283 | 7/1984 | Harvey et al. | 424/57 |
| 4,522,806 | 6/1985 | Muhlemann et al. | 424/52 |
| 4,526,778 | 7/1985 | Harvey et al. | 424/52 |
| 4,562,063 | 12/1985 | Hayes et al. | 424/49 |
| 4,562,065 | 12/1985 | Hayes et al. | 424/49 |
| 4,562,066 | 12/1985 | Hayes et al. | 424/52 |
| 4,647,452 | 3/1987 | Ritchey et al. | 424/54 |
| 4,684,528 | 8/1987 | Godfrey | 424/74 |
| 4,758,439 | 7/1988 | Godfrey | 424/74 |
| 4,814,163 | 3/1989 | Barth | 424/49 |
| 4,814,164 | 3/1989 | Barth et al. | 424/49 |
| 4,826,676 | 5/1989 | Gioffre et al. | 424/52 |
| 4,863,722 | 9/1989 | Rosenthal | 424/49 |
| 4,937,066 | 6/1990 | Vlock | 424/52 |
| 5,059,416 | 10/1991 | Cherukuri et al. | 424/48 |
| 5,085,850 | 2/1992 | Pan et al. | 424/49 |
| 5,188,820 | 2/1993 | Cummins et al. | 424/49 |

*Primary Examiner*—Shep K. Rose
*Attorney, Agent, or Firm*—Charles B. Barris

[57] ABSTRACT

Zinc oxide particles, preferably agglomerated, are added to dentifrices such as toothpastes, tooth gels, or tooth powders to inhibit the formation of plaque. The dentifrices contain sodium bicarbonate and other conventional ingredients such as thickeners, anti-calculus agents such as a pyrophosphate salts, anti-caries agent such as sodium fluoride, flavorings, sweetening agents, and/or secondary abrasives.

7 Claims, No Drawings

DENTIFRICES CONTAINING ZINC OXIDE PARTICLES AND SODIUM BICARBONATE

FIELD OF THE INVENTION

The present invention relates to dentifrices, e.g., toothpastes, gels and tooth powders, which provide anti-plaque, anti-tartar, and gingivitis preventative effects.

BACKGROUND OF THE INVENTION

Calculus, or tartar as it is sometimes called, is the solid, hard mass of calcified material deposited on and adhering to the surfaces of the teeth. Calculus is composed of inorganic salts which make the calculus hard and resistant. Calculus is largely calcium phosphates, mainly hydroxyapatite with varying, but small, amounts of other inorganic salts.

Although not entirely understood, the general concept is that deposits, mostly plaque, which is a sticky film of oral bacteria and their products, become calcified with the ultimate formation on the teeth of a hard mineral consisting of calcium hydroxyapatite.

As the mature calculus develops, it becomes visibly white or yellowish in color unless stained or discolored by some extraneous agent. In addition to being unsightly and undesirable from an aesthetic standpoint, the mature calculus deposits can be constant sources of irritation of the gingiva.

Methods for chemically reducing or preventing calculus formation have been directed at affecting the process at any of several stages in its development. One approach is to develop agents which inhibit the formation of the crystalline calcium phosphate or hydroxyapatite.

A wide variety of chemical and biological agents have been suggested to retard calculus formation or to remove calculus after it is formed. The chemical approach to calculus inhibition generally involves crystal growth inhibition which prevents the calculus from forming. Generally, once formed, mechanical removal by the dentist is necessary and is a routine dental office procedure.

The most widely used tartar control agents in dentifrices are the pyrophosphate salts. A disadvantage of pyrophosphate salts is that they cause irritation in some users and in other users they cause sensitivity to the teeth.

Prevention of plaque and gingivitis can be very important to the health of individuals. Loss of teeth and other ill affects can result from poor oral health.

Gingivitis is an inflammation or soreness of the exposed gums and gingiva and is usually caused by bacteria in plaque. In mild cases the only symptom is a slight reddening of the gum tissues at the tip of the gingiva. In more severe cases the reddening spreads and the gums become swollen. Sometimes the gums bleed on brushing or when probed by a dentist. In very severe cases spontaneous bleeding of the gums occurs.

Gingivitis can often be inhibited by regular, twice daily brushing with a regular toothpaste and by the use of floss to remove plaque from between teeth. Sometimes, however, over-the-counter chemotherapeutic agents such as anti-bacterial mouthwashes or toothpastes containing anti-bacterial agents are useful in preventing gingivitis in more susceptible individuals.

Many kinds of anti-bacterial agents, when incorporated into mouthwashes or dentifrices, have been found to be at least somewhat effective in preventing gingivitis. A mouthwash containing the essential oils thymol, eucalyptus, and menthol in an alcohol/water base is currently marketed and has been shown in several clinical studies to provide a significant benefit. This product, however, has an unpleasant taste which deters use. Toothpastes containing triclosan have also been shown to be effective and are available in Europe. Cationic anti-microbial surfactants have also been suggested as anti-plaque/anti-gingivitis agents.

Enhancement of the activity of triclosan and cationic anti-microbials by zinc salts has also been reported; however, due to the unpleasant lingering taste of zinc salts, only minor levels of zinc salts have been used. Since one would expect any microbial effect of zinc salts to be due to the release of zinc ions, one would not expect insoluble zinc compounds to be effective anti-bacterials.

Gingivitis is a significant disease because it is believed that in some cases it can lead to or be a precursor to more serious gum diseases known as periodontitis.

Periodontitis is a disease which occurs below the gum line. Anaerobic bacteria collect in pockets formed between the teeth and gums, and the gums recede from teeth when serious inflammation of the gums is present, loss of alveolar bone often occurs and the patient is often at risk of loosing teeth. Periodontitis cannot generally be treated by superficial use of chemotherapeutic agents. The intervention of a dentist is required and surgery is often necessary.

Zinc oxide is used in a number of human health products. In the dental application area, it is used in dental fillings, dental cements, and dental impression materials, and it is suggested for use in a calcium hydroxide-based paste to establish an alkaline barrier inhibiting bacterial attack without gingival and periodontal irritation (see U.S. Pat. No. 4,375,968 issued Mar. 8, 1983 to M. J. Manhart). The strong alkaline properties of the calcium hydroxide are controlled by using a two part paste and mixing before use. The zinc oxide is added as a filler to the calcium hydroxide-containing first part as a moderator to slow the setting time of the final paste to about four minutes.

There is still a need for improved dentifrices which help prevent gingivitis and tartar and plaque build-up.

SUMMARY OF THE INVENTION

The present invention provides a dentifrice in the form of a toothpaste, a gel, or a powder. The toothpaste or gel comprise sodium bicarbonate, typically about 3–70%, preferably about 10–65%; an effective amount of zinc oxide particles, preferably agglomerated submicron zinc oxide particles; and a liquid in an amount sufficient to provide the desired consistency. The amount of zinc oxide particles is typically about 0.1–10%, preferably about 1–5%.

As used herein, the term "effective amount" means the amount which is sufficient to achieve the desired effect or result. The amount of zinc oxide particles which is effective is that amount which provides an anti-microbial effect, which will depend upon whether or not a secondary anti-microbial agent is used.

In a toothpaste, the liquid vehicle may comprise water and humectant, typically in an amount ranging from about 10–90%. Water is a desirable component when a toothpaste or tooth gel is being prepared. Water comprises up to about 50%, preferably about 5–35% of the composition. However, an anhydrous toothpaste or gel can be formulated if desired. A humectant is also a desirable component in a toothpaste or gel. Preferably, the humectant comprises about 5–50% of the formulation, preferably about 5–35%. In translucent gels, where the refractive index is an important consideration, it is preferred to use higher ratios of humectant to water than in opaque pastes. For a gel the ratio of humectant to water should be above about 0.5 to 1, preferably above 1 to 1.

To improve clarity when the dentifrice is a gel, less sodium bicarbonate is used, typically about 3–60%, preferably about 5–35% and coarser bicarbonate crystals are chosen, preferably crystals having an average particle size of greater than 44 microns, most preferably greater than 74 microns. If a secondary abrasive is used, the abrasive selected is one which will give a clear or translucent gel.

Optional, but preferred, components which are included in the dentifrices are organic thickeners and/or inorganic thickeners, surfactants, flavoring agents and/or sweetening agents, coloring agents and/or pigments, a secondary abrasive, a secondary anti-microbial agent, an additional anti-calculus agent such as a pyrophosphate salt, an anti-caries agent such as a soluble fluoride source which is compatible with zinc oxide, buffering agents such as alkali metal orthophosphates, phosphoric acid, alkali metal glycerophosphates, tartrates and citrates, and like components conventionally added to toothpastes and tooth gels.

The tooth powder comprises sodium bicarbonate, typically about 20–95%, preferably above about 50%, and an effective amount of zinc oxide particles, preferably agglomerated zinc oxide particles. The amount of zinc oxide particles is typically about 0.1–10%, preferably about 1–5%. Optional, but preferred, components which are included in the tooth powder are a surfactant, a secondary abrasive, a secondary anti-microbial agent, a flavoring agent and/or a sweetening agent, a secondary anti-calculus agent such as a pyrophosphate salt, and an anti-caries agent such as a soluble fluoride source which is compatible with zinc oxide, and one or more processing aids such as a flow aid to insure product uniformity.

The present invention further provides a method of preventing plaque, calculus, and/or gingivitis by adding to a dentifrice selected from the group consisting of a toothpaste, a gel, and a tooth powder, about 0.1–10% of zinc oxide, preferably 1–5%, as an anti-plaque, anti-gingivitis, anti-bacterial and/or tartar formation inhibiting agent.

One skilled in the art would expect that the zinc needs to be provided in a soluble state to be most effective; however, the more soluble zinc salts, while effective, have a lingering unpleasant metallic and astringent taste. At the pH of dentifrices containing sodium bicarbonate, i.e., a pH of about 7.5–9.5, zinc oxide has minimum solubility. Thus, it is surprising that the zinc oxide provides the desired protection and that the lingering unpleasant metallic and astringent taste of zinc is absent. It is believed that the zinc oxide particles remain trapped in the plaque and are released to kill the bacteria and prevent tartar formation only when needed as the pH drops due to bacterial metabolism.

DESCRIPTION OF THE PREFERRED EMBODIMENTS

Zinc oxide having a particle size of 50 microns or less is preferred and particles having a size of 5 microns or less are most preferred. Specific, but non-limiting, examples of zinc oxide having sub-micron average particle sizes are available from Sachtleben Chemie under the trademark Sachtotec. The particles have an average particle size of about 0.20 micron and the particle size can be as low as 0.005–0.015 micron.

Preferably, the sodium bicarbonate particles have a mean particle size of about 5 to 200 microns. The bicarbonate particles may be incorporated in the dentifrice in varying amounts, depending upon the desired properties of the formulation. Higher levels of sodium bicarbonate, e.g., about 50%, allow it to be used as the sole abrasive. Such formulations remove plaque effectively, have a desirable low abrasivity, and provide an exceptionally clean feeling to the teeth and gums after brushing. Lower levels allow the incorporation of secondary abrasives and permit the formulation of clearer gels. At very low levels, e.g., less than about 10%, the bicarbonate still provides effective buffering in the pH 7.5 to 9.5 range and enhances the clean feeling of the teeth and gums, but to a lesser degree than when high levels are used.

Suitable humectants include glycerine, propylene glycol, sorbitol, polypropylene glycol and/or polyethylene glycol (e.g., molecular weight of 400–1200), and/or the like. Also advantageous are liquid mixtures of water, glycerine and sorbitol or mixtures with polyethylene glycol.

In addition to the above described required components, the dentifrices can contain a variety of conventionally used optional components.

Toothpastes and gels typically contain a natural or synthetic organic thickener or gelling agent in proportions of about 0.1–10%, preferably about 0.3–2%. Suitable organic thickeners include sodium carboxymethyl cellulose, starch, gum tragacanth, carrageenan, xanthan gum, polyacrylate salts, polyvinylpyrrolidone, hydroxyethylpropyl cellulose, hydroxybutylmethyl cellulose, hydroxypropylmethyl cellulose, or hydroxyethyl cellulose, which are usually used in amounts of about 0.1–2.0%. Inorganic thickeners such as hydrated silicas may also be used in amounts of about 0.5–10% or greater.

Conventional abrasives or polishing materials are also useful herein as a secondary abrasive. Useful water-insoluble abrasives include sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, aluminum silicate, zirconium silicate, hydrated silica, hydrated alumina, bentonite, and/or the like.

Preferred abrasive materials which may be admixed with the sodium bicarbonate include hydrated silica, silica gel, or colloidal silica and complex amorphous alkali metal aluminosilicates. When visually clear gels are employed, polishing agents of hydrated or colloidal silica, alkali metal aluminosilicate complexes, and alumina are particularly useful since they have refractive indices close to the refractive indices of the gelling agent-liquid systems (including water and/or humectant) commonly used in the gels.

Any of the foregoing water-insoluble abrasives may be present in amounts of up to about 50%, preferably in amounts up to about 20%, which amount will depend upon the amount of sodium bicarbonate used.

Organic surfactants are useful herein to achieve increased cleaning action, to assist thorough and complete dispersion of the anti-calculus agent throughout the oral cavity, and to improve the detergent and foaming properties of the dentifrices. Anionic, nonionic or ampholytic surfactants may be used.

Examples of suitable anionic surfactants are the water-soluble salts of the higher alkyl sulfates such as sodium lauryl sulfate or other $C_8$-$C_{18}$ alkyl sulfates, water-soluble salts of higher fatty acid monoglyceride monosulfates such as the sodium salt of the monosulfate monoglyceride of hydrogenated coconut oil fatty acids, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds such as $C_{12}$-$C_{16}$ fatty acids, alkyl or acyl radicals, and the like. Examples of the last mentioned amides are N-lauryl sarcosinate and the sodium, potassium, and ethanolamine salts of N-lauroyl, N-myristoyl, or N-palmitoyl sarcosinate which should be substantially free from soap or similar higher fatty acid materials.

Other suitable surfactants include non-ionic agents such as the condensates of sorbitan monostearate with ethylene oxide, the condensates of ethylene oxide with propylene oxide, or the condensates of propylene glycol (available under the trademark "Pluronics"). Other examples of water-soluble nonionic surfactants useful herein are the condensation products of ethylene oxide with various other compounds which are reactive therewith and have long hydrophobic chains (e.g., $C_{12}$-$C_{20}$ aliphatic chains) which condensation products ("ethoxamers") contain hydrophilic polyoxyethylene moieties, such as condensation products of polyethylene oxide with fatty acids, fatty alcohols, fatty amides, or polyhydric alcohols (e.g., sorbitain monostearate).

The various surfactants may be utilized alone or in admixture with one another. In toothpastes, the total amount used is preferably about 0.05%-5%, more preferably about 0.1%-2.0%.

Sweetening agents are also useful herein. They include saccharin, sucralose, dextrose, levulose, aspartame, D-tryptophan, dihydrochalcones, acesulfame, sodium cyclamate, and calcium cyclamate. They are generally used in amounts of about 0.1-4%.

Secondary anti-microbial agents can be included in the dentifrices to help inhibit plaque formation and gingivitis or to reduce mouth odor. For example, cationic anti-microbial agents such as cetyl pyridinium chloride or benzothonium chloride can be used. Bis-biguanides are also effective. Such agents include chlorhexidine (1,6-bis [$N^5$-p-chlorophenyl-N-biguanido]hexane), and the soluble and insoluble salts thereof and related materials such as 1,2-bis($N^5$-p-trifluoromethylphenyl-$N^1$-biguanido)ethane which are described more fully in U.S. Pat. No. 3,923,002 (issued Jan. 20, 1976 to Haefale), U.S. Pat. No. 3,937,807 (issued Feb. 10, 1976 to Haefale), Belgian Pat. No. 843,244 (published Dec. 22, 1976) and Belgian Pat. No. 844,764 (published Jan. 31, 1977). If present, the secondary anti-microbials generally comprise about 0.01-0.5% of the composition. When using cationic agents, it is generally necessary to avoid using anionic surfactants in the formulation. Non-ionic anti-microbials such as triclosan can be used. These materials have the advantage of not losing efficacy in the presence of anionic surfactants.

Soluble complex phosphate salts such as pyrophosphates, tripolyphosphates, and hexametaphosphates, may be added as secondary anti-calculus agents. The pyrophosphates include mono-, di-, tri- or tetraalkali metal pyrophosphates and mixtures thereof. The preferred pyrophosphate salts include disodium pyrophosphate, dipotassium pyrophosphate, tetrasodium pyrophosphate, and/or tetrapotassium pyrophosphate. The pyrophosphates may be employed in their anhydrous or hydrated forms. Although a particular pyrophosphate salt, e.g., disodium pyrophosphate, may be the pyrophosphate initially added to the formulation, the actual pyrophosphate ion present in the composition and the quantity present in the dentifrice is dependent on both the final pH of the dentifrice and the salting-out effect of the sodium bicarbonate. If desired, pyrophosphates are added to the dentifrices in an amount from about 0.5-10%, typically 1-6%.

The dentifrices can include a water-soluble fluoride ion source which is effective both as a pyrophosphatase inhibitor and as an anti-caries agent. Suitable fluoride ion sources include inorganic fluoride salts such as soluble alkali metal or alkaline earth metal salts, e.g., sodium fluoride, potassium fluoride, sodium fluorosilicate, ammonium fluorosilicate, sodium fluorozirconate or sodium monofluorophosphate. Alkali metal fluorides such as sodium fluoride, sodium monofluorophosphate, and mixtures thereof are preferred.

The amount of the soluble fluoride ion source in the dentifrice is dependent on the particular compounds used and the type of dentifrice, but it must be incorporated in an effective but nontoxic amount, generally up to about 5.0%. Any suitable minimum amount of fluoride may be used, but it is preferable to employ a quantity sufficient to release about 50 to 3500 ppm, preferably about 850-1500 ppm, of fluoride ions. In the case of sodium fluoride, the fluoride ion source is present in an amount from 0.05-0.65%, preferably about 0.18-0.35%. In the case of sodium monofluorophosphate, the amount is about 0.2-2%, more typically about 0.65%-1.20%.

Dentifrices containing zinc oxide particles and sodium bicarbonate mixtures with other conventional dentifrice components exhibit enhanced anti-calculus properties. It is believed that zinc ions are released from zinc oxide particles trapped in plaque when the bacteria in plaque metabolize sugars and release acids. The zinc ions are believed to inhibit nucleation of calcium phosphate crystals and thus prevent tartar from forming. Zinc ions have an advantage over pyrophosphate salts in the prevention of tartar in that pyrophosphate hydrolyzes in saliva to inactive orthophosphate.

Various other materials may be incorporated in the dentifrices. Examples thereof are coloring and whitening agents, preservatives, silicones, and/or chlorophyll compounds. These adjuvants are incorporated in the dentifrices in amounts which do not substantially adversely affect the properties and characteristics desired and are selected and used in effective amounts, depending upon the particular adjuvant and type of dentifrice involved.

The pH of the dentifrices herein range from 7.0 to 10.0, preferably from 7.5 to 9.0. The pH is preferably achieved through a proper balancing of the bicarbonate and other additives.

The dentifrices herein are made using conventional mixing techniques and used in a conventional manner.

The following examples further illustrate the present invention, but it is understood that the invention is not limited thereto. All amounts and proportions referred to herein and in the appended claims are by weight and temperatures are in degrees Celsius unless otherwise indicated.

EXAMPLES 1-7

The following are representative toothpastes.

|  | 1 | 2 | 3 | 4 | 5 | 6 | 7 |
|---|---|---|---|---|---|---|---|
| Zinc oxide[1] | 2.000 | 4.000 | 1.000 | 0.500 | 2.000 | 2.000 | 5.000 |
| Sodium bicarbonate | 63.160 | 60.080 | 54.450 | 62.920 | 54.210 | 49.210 | 27.927 |
| Tetrasodium pyrophosphate | — | — | 5.350 | — | 5.350 | 5.350 | 5.350 |
| Calcium pyrophosphate | — | — | — | — | — | — | 10.000 |
| Sodium fluoride | — | — | — | 0.243 | 0.243 | 0.243 | 0.243 |
| Sodium monofluorophosphate | — | 0.780 | 0.780 | — | — | — | — |
| Glycerin | 14.070 | 15.070 | 14.070 | 14.070 | 14.070 | 14.070 | 4.100 |
| Polyethylene glycol[2] | 1.000 | — | 1.000 | 1.000 | — | 1.000 | 1.000 |
| Carboxymethyl cellulose | 0.850 | 0.850 | 0.650 | 0.850 | 0.650 | 0.650 | 0.700 |
| Water | 16.112 | 16.112 | 20.100 | 17.609 | 20.877 | 24.877 | 5.280 |
| Sodium saccharin | 1.208 | 1.208 | 1.000 | 0.808 | 0.800 | 0.800 | 1.000 |
| Sorbitol | — | — | — | — | — | — | 37.100 |
| Sodium lauryl sulfate | 0.300 | 0.300 | 0.300 | 1.000 | — | 0.600 | 0.300 |
| Sodium lauroyl sarcosinate (30%) | 0.300 | 0.600 | 0.300 | — | 0.600 | — | 1.000 |
| Flavor | 1.000 | 1.000 | 1.000 | 1.000 | 1.200 | 1.200 | 1.000 |
|  | 100.000 | 100.000 | 100.000 | 100.000 | 100.000 | 100.000 | 100.000 |

[1]Primary particle size of <1 micron agglomerated to a median particle size of about 6.4 microns
[2]PEG-8

EXAMPLES 8-14

The following are representative tooth gels:

|  | 8 | 9 | 10 | 11 | 12 | 13 | 14 |
|---|---|---|---|---|---|---|---|
| Zinc oxide[1] | 2.000 | 4.000 | 1.000 | 2.000 | 2.000 | 2.000 | 2.000 |
| Sodium bicarbonate | 27.245 | 24.515 | 21.245 | 30.547 | 21.047 | 21.047 | 5.422 |
| Tetrasodium pyrophosphate | — | — | 5.350 | — | 5.350 | 9.350 | 2.000 |
| Sodium fluoride | — | — | — | 0.243 | 0.243 | 0.243 | 0.243 |
| Sodium monofluorophosphate | — | 0.780 | 0.780 | — | — | — | — |
| Glycerin | 17.000 | 17.000 | 16.220 | 14.745 | 14.745 | 14.745 | 9.100 |
| Sorbitol (10% Solution) | 20.290 | 20.290 | 20.290 | 27.500 | 17.500 | 17.500 | 50.100 |
| Polyethylene glycol[2] | 1.000 | 1.000 | 1.000 | 1.000 | 1.000 | 1.000 | 1.000 |
| Carboxymethyl cellulose | 0.650 | 0.600 | 0.600 | 0.600 | 0.600 | 0.600 | 0.600 |
| Water | 16.810 | 16.810 | 18.360 | 8.360 | 18.360 | 18.360 | 9.080 |
| Sodium saccharin | 0.500 | 0.500 | 0.650 | 0.500 | 0.650 | 0.650 | 0.350 |
| Abrasive hydrated silica[3] | 8.000 | 8.000 | 8.000 | 8.000 | 12.000 | 8.000 | 13.000 |
| Thickening silica[4] | 4.500 | 4.500 | 4.500 | 4.500 | 4.500 | 4.500 | 4.500 |
| Sodium lauryl sulfate | 1.000 | 1.000 | 0.500 | 0.500 | 1.000 | 1.000 | 0.500 |
| Sodium lauroyl sarcosinate (30%) | — | — | 0.500 | 0.500 | — | — | 1.600 |
| Flavor | 1.000 | 1.000 | 1.000 | 1.000 | 1.000 | 1.000 | 0.500 |
| Color | 0.005 | 0.005 | 0.005 | 0.005 | 0.005 | 0.005 | 0.005 |
|  | 100.000 | 100.000 | 100.000 | 100.000 | 100.000 | 100.000 | 100.000 |

[1]Primary particle size of <1 micron agglomerated to a median particle size of about 6.4 microns
[2]PEG-8
[3]Sylodent 700
[4]Sylox 2

EXAMPLES 15-20

The following are representative tooth powders:

|  | 15 | 16 | 17 | 18 | 19 | 20 |
|---|---|---|---|---|---|---|
| Zinc oxide[1] | 2.000 | 4.000 | 1.000 | 2.000 | 5.000 | 2.000 |
| Sodium bicarbonate | 95.900 | 93.020 | 91.120 | 90.307 | 87.157 | 82.557 |
| Calcium pyrophosphate | — | — | — | 5.000 | — | — |
| Tetrasodium pyrophosphate | — | — | 5.350 | — | 5.350 | 5.350 |
| Sodium monofluorophosphate | — | 0.780 | 0.780 | — | — | — |

-continued

|  | 15 | 16 | 17 | 18 | 19 | 20 |
|---|---|---|---|---|---|---|
| Sodium fluoride | — | — | — | 0.243 | 0.243 | 0.243 |
| Flavor | 1.000 | 1.000 | 1.000 | 0.800 | 1.000 | 1.200 |
| Sodium saccharin | 0.500 | 0.500 | 0.650 | 0.850 | 0.650 | 0.650 |
| Magnesium oxide | 0.100 | 0.200 | 0.100 | 0.300 | 0.100 | — |
| Sodium lauryl sulfate | 0.500 | 0.500 | — | 0.500 | 0.500 | — |
| Abrasive hydrated silica[2] | — | — | — | — | — | 8.000 |
|  | 100.000 | 100.000 | 100.000 | 100.000 | 100.000 | 100.000 |

[1]Primary particle size of <1 micron agglomerated to a median particle size of about 6.4 microns
[2]Sylodent 700

The above compositions are effective in reducing calculus and preventing gum disease. In addition, they possess acceptable cosmetic properties.

EXAMPLE 21

The following example shows the advantage of incorporating zinc oxide having a median particle size of 6.4 microns into a toothpaste formulation containing baking soda.

Arm & Hammer Dental Care toothpaste and Arm & Hammer Dental Care toothpaste containing 2% added zinc oxide particles were mixed in water and compared for anti-plaque efficacy in an in vitro plaque growth model with zinc oxide particles alone and chlorhexidine alone. The zinc oxide particles had a primary particle size of <1 micron and the particles were agglomerated to a median particle size of about 6.4 microns.

In the model, $S.$ $mutans$ was grown up in Brain heart infusion medium containing 3% sucrose into which glass rods were suspended. After overnight growth the glass rods with adherent plaque were immersed for 60 seconds in the anti-plaque test solutions and immersed for 30 seconds in a water rinse. The rods were then resubmerged in fresh daily growth medium for 6 hours at 37° C. The rods were retreated with the anti-plaque test solutions and rinsed and then stored overnight in saliva at 37° C. The treatment and growth cycles were repeated to complete a total of three full cycles, after which the dry weight of the plaque formed on the rods was determined. The results are shown below.

|  | % Plaque Reduction |
|---|---|
| Water | 0 |
| Arm & Hammer Dental Care Toothpaste | 21 |
| Arm & Hammer Dental Care Toothpaste with 2% Zinc Oxide Particles | 70 |
| Chlorhexidine (0.12%) | 74 |
| Zinc oxide particles (0.5%) | 64 |

The toothpaste containing zinc oxide showed statistically ($p < 0.05$) superior anti-plaque performance to zinc oxide particles alone. The performance of the toothpaste containing zinc oxide particles was indistinguishable from the anti-plaque performance of chlorhexidine.

In addition to the levels and combinations of ingredients shown in these examples, others can be used which are consistent with the invention disclosed and claimed herein.

What is claimed is:

1. A dentifrice in the form of a toothpaste or tooth gel comprising:

a. about 3–70% sodium bicarbonate;
   b. an effective amount of zinc oxide particles; and
   c. a liquid vehicle in an amount sufficient to provide the desired consistency, said dentifrice being free of more soluble zinc salts and their lingering unpleasant metallic and astringent taste, said zinc oxide particles being agglomerated and having a medium particle size of 50 microns or less and being agglomerated from zinc oxide primary particles having sub-micron average particle size, and whose release of zinc ions is effective primarily as an antiplaque, anti-gingivitis, antibacterial and tartar formation inhibiting agent and whose release to kill the bacteria and prevent tartar formation is free from the lingering unpleasant metallic and astringent taste of most zinc salts when they are also absent.

2. The dentifrice of claim 1 in the form of a toothpaste, wherein the sodium bicarbonate is about 10–65%, the zinc oxide particles are about 0.1–10%, and the liquid vehicle is water in an amount of up to about 50%.

3. The dentifrice of claim 2, wherein the sodium bicarbonate is about 40–65%, the zinc oxide particles are agglomerated particles present in an amount of about 1–5%, and the water is about 5–35%.

4. The dentifrice of claim 1 in the form of a gel, wherein the sodium bicarbonate is about 3–60%, the zinc oxide particles are about 0.1–10%, and the liquid vehicle is water in an amount of up to about 50%.

5. The dentifrice of claim 4, wherein the sodium bicarbonate is about 5–35%, the zinc oxide particles are agglomerated zinc oxide particles present in an amount of about 1–5%, and the water is about 5–20%.

6. A method of inhibiting plaque formation by adding to a dentifrice containing sodium bicarbonate, which is selected from the group consisting of a toothpaste, and a gel, about 0.1–10% by weight of zinc oxide particles, said dentifrice being free of more soluble zinc salts and their lingering unpleasant metallic and astringent taste, said zinc oxide particles being agglomerated and having a medium particle size of 50 microns or less and being agglomerated from zinc oxide primary particles having sub-micron average particle size, and whose release of zinc ions is effective primarily as an antiplaque, anti-gingivitis, antibacterial and tartar formation inhibiting agent and whose release to kill the bacteria and prevent tartar formation is free from the lingering unpleasant metallic and astringent taste of most zinc salts when they are also absent.

7. The method of claim 6, wherein the zinc oxide particles are agglomerated particles present in an amount of about 1–5%.

* * * * *